United States Patent
Cassidy

(10) Patent No.: US 7,741,815 B2
(45) Date of Patent: Jun. 22, 2010

(54) LITHIUM POLYMER BATTERY POWERED INTRAVENOUS FLUID WARMER

(75) Inventor: David Cassidy, Chelmsford, MA (US)

(73) Assignee: General Electric Company, Schenectady, NY (US)

(*) Notice: Subject to any disclaimer, the term of this patent is extended or adjusted under 35 U.S.C. 154(b) by 818 days.

(21) Appl. No.: 11/593,456

(22) Filed: Nov. 6, 2006

(65) Prior Publication Data

US 2007/0105010 A1 May 10, 2007

Related U.S. Application Data

(60) Provisional application No. 60/734,108, filed on Nov. 7, 2005.

(51) Int. Cl.
*H02J 7/04* (2006.01)

(52) U.S. Cl. .................. 320/152; 320/150; 320/134; 320/136; 392/480; 392/479; 219/520; 219/535

(58) Field of Classification Search .............. 320/150, 320/152, 136, 134
See application file for complete search history.

(56) References Cited

U.S. PATENT DOCUMENTS

| | | | | |
|---|---|---|---|---|
| 4,314,143 A * | 2/1982 | Bilstad et al. | ............... | 219/497 |
| 4,709,202 A * | 11/1987 | Koenck et al. | ............... | 320/112 |
| 4,845,419 A * | 7/1989 | Hacker | ............... | 320/136 |
| 5,408,577 A * | 4/1995 | Weber et al. | ............... | 392/480 |
| 5,568,039 A * | 10/1996 | Fernandez | ............... | 320/150 |
| 5,583,415 A * | 12/1996 | Fernandez et al. | ............ | 320/121 |
| 5,680,027 A * | 10/1997 | Hiratsuka et al. | ............. | 320/106 |
| 5,680,031 A | 10/1997 | Pavlovic et al. | | |
| 5,767,659 A * | 6/1998 | Farley | ............... | 320/106 |
| 6,142,974 A | 11/2000 | Kistner et al. | | |
| 6,175,688 B1 * | 1/2001 | Cassidy et al. | .............. | 392/470 |
| 6,229,957 B1 * | 5/2001 | Baker | ............... | 392/470 |
| 6,236,809 B1 * | 5/2001 | Cassidy et al. | .............. | 392/470 |
| 6,271,645 B1 * | 8/2001 | Schneider et al. | .......... | 320/118 |
| 6,480,257 B2 * | 11/2002 | Cassidy et al. | .............. | 392/470 |

(Continued)

FOREIGN PATENT DOCUMENTS

WO 9939400 A1 8/1999

(Continued)

OTHER PUBLICATIONS

Dallas Semiconductor DS1086 Spread-Spectrum EconOscillator Data sheet, Sep. 2003.*

*Primary Examiner*—Edward Tso
*Assistant Examiner*—Manuel Hernandez
(74) *Attorney, Agent, or Firm*—Alan Taboada; Moser IP Law Group

(57) ABSTRACT

A lithium polymer (LiPo) battery pack having LiPo battery cells is provided which includes battery protection circuitry, charging circuitry, cell balancing circuitry, and control and communication circuitry. The batteries can be charged while in use by an internal charger. Battery charging and discharging are accomplished in a controlled and protected manner to avoid overcharging and overdischarging conditions. The novel battery pack has built-in safeguards against dangerous LiPo battery conditions and is implemented in a small, portable unit which contains the battery cells, control and protection circuitry, internal charger and display gauge. The battery pack is useful for powering an intravenous fluid warmer or other medical or electrical devices and equipment.

21 Claims, 5 Drawing Sheets

U.S. PATENT DOCUMENTS

| | | | |
|---|---|---|---|
| 6,495,992 B1 * | 12/2002 | Pavlovic | 320/161 |
| 6,534,951 B2 | 3/2003 | Kawashima | |
| 6,641,556 B1 | 11/2003 | Shigezawa | |
| 6,664,000 B1 | 12/2003 | Sonobe | |
| 6,747,561 B1 * | 6/2004 | Reeves | 340/573.1 |
| 7,031,602 B2 * | 4/2006 | Faries et al. | 392/470 |
| 7,514,903 B2 * | 4/2009 | Lee | 320/150 |
| 2001/0011585 A1 * | 8/2001 | Cassidy et al. | 165/46 |
| 2004/0096732 A1 | 5/2004 | Shin et al. | |
| 2004/0140898 A1 * | 7/2004 | Reeves | 340/573.1 |
| 2004/0170409 A1 * | 9/2004 | Faries et al. | 392/470 |
| 2005/0161588 A1 | 7/2005 | Kominsky et al. | |

FOREIGN PATENT DOCUMENTS

WO 2005009500 A2 2/2005

* cited by examiner

LITHIUM POLYMER BATTERY POWERED INTRAVENOUS FLUID WARMER

CROSS REFERENCE TO RELATED APPLICATIONS

The present application claims priority under 35 U.S.C. 119(e) of U.S. Provisional Patent Application titled LITHIUM POLYMER BATTERY PACK, Application No. 60/734,108 filed on Nov. 7, 2005.

TECHNICAL FIELD OF THE INVENTION

This invention is generally related to battery-operated fluid warmers and, in particular, to fluid warmers running on batteries including lithium polymer rechargeable cells.

STATEMENT REGARDING FEDERALLY SPONSORED RESEARCH OR DEVELOPMENT

Not applicable

BACKGROUND OF THE INVENTION

Intravenous (IV) fluid warmers have traditionally been powered by an AC power source because of the high power required to heat IV fluids. Battery powered IV fluid warmers have heretofore had poor performance because of the battery sources which have been available.

The battery requirements for IV fluid warmers include the following:
1. Small size and weight for easy portability,
2. Extremely high discharge rates (very low impedance),
3. Protection from overcharging,
4. Protection from overdischarging,
5. Capability to heat at least four liters of IV fluids, and
6. Battery "gas gauge" (Battery Condition Indicator) to monitor battery charge status.

A known battery powered IV fluid warmer is called the Thermal Angel and is produced by Estill Medical. Thermal Angel uses a 12 volt lead acid battery which is heavy, weighing about 7 pounds, limiting its portability. The battery requires an external charger and thus requires an extra piece of equipment for operational use Thermal Angel has a low heating capacity of less than 2 liters of room temperature IV fluid. It cannot be charged while the fluid warmer is in use. It has a long charge time of about 12 hours and cannot be fast charged. In addition, the device has only a minimal gas gauge which is only accurate when the battery is not in use.

Lithium polymer (LiPo) batteries have extremely low internal impedance and are particularly suitable for high current applications. They have very high energy density, do not exhibit memory effects, and in addition, are environmentally safe. However, such batteries can be dangerous if overcharged or overdischarged and in such circumstances the batteries can explode or catch fire.

BRIEF SUMMARY OF THE INVENTION

In accordance with the present invention, lithium polymer (LiPo) battery cells are employed in a portable unit which includes battery protection circuitry, charging circuitry, cell balancing circuitry, and control and communication circuitry. The batteries can be charged while in use by an internal charger. Battery charging and discharging are accomplished in a controlled and protected manner to avoid overcharging and overdischarging conditions. The novel battery pack has built-in safeguards against dangerous LiPo battery conditions and is implemented in a small, portable unit which contains the battery cells, control and protection circuitry, internal charger and display gauge. The battery pack or the battery cells may be enclosed in an enclosure resistant to fire and/or explosion.

An embodiment of the present invention is described herein for powering a fluid warmer for intravenous or similar fluids. It is contemplated that the present invention may also be employed as a power source for powering other medical equipment or electrical equipment more generally.

BRIEF DESCRIPTION OF THE SEVERAL VIEWS OF THE DRAWINGS

Further aspects of the invention will be apparent upon consideration of the following detailed description, taken in conjunction with the accompanying drawings, in which like reference characters refer to like parts throughout, and in which.

DETAILED DESCRIPTION OF THE INVENTION

The fluid warmer assembly of the present invention is useful for powering an IV fluid warmer used in military and civilian emergency settings, such as a battlefield or civilian medical facility. DC power for charging the fluid warmer assembly can be provided from a vehicle or other battery source operating over a typical voltage range of 12-36 volts DC. An interconnecting cable can provide an electrical connection between an external DC power source and the fluid warmer assembly. In one embodiment, a hermaphrodite cable may be provided so that only a single cable having associated connectors is necessary to make a connection between the fluid warmer assembly and a power source. Such hermaphrodite connectors have no "wrong end" and either connector end can be plugged into the fluid warmer assembly and the power source.

The fluid warmer assembly according to the present invention provides a unitary device which contains the battery cells, control and monitoring circuitry and charging circuitry needed for reliable and safe operation without a need for auxiliary or additional equipment. The fluid warmer assembly may have a replaceable heater cartridge inside the fluid warmer. The replaceable heater cartridge includes a case through which an intravenous fluid line or a tube extends. Components in contact with the fluid may optionally be of a single-use design considering a convenient use or medically hazardous conditions. The fluid warmer assembly is capable of an intelligent power control within safe operating limits of the exemplary LiPo cells.

Data from the fluid warmer assembly can typically represent the following parameters:
Nominal voltage,
Battery capacity and amp/hours, Maximum current draw, and Low voltage cut out level.

Battery temperature is monitored to determine the proper load or charging parameters. An audible alarm can be provided in the fluid warmer assembly to signify a fully discharged state and/or a hazard state. Multicolor LEDs can be included to show, for example, a change from red to green to indicate the state of charge.

Figure 1:
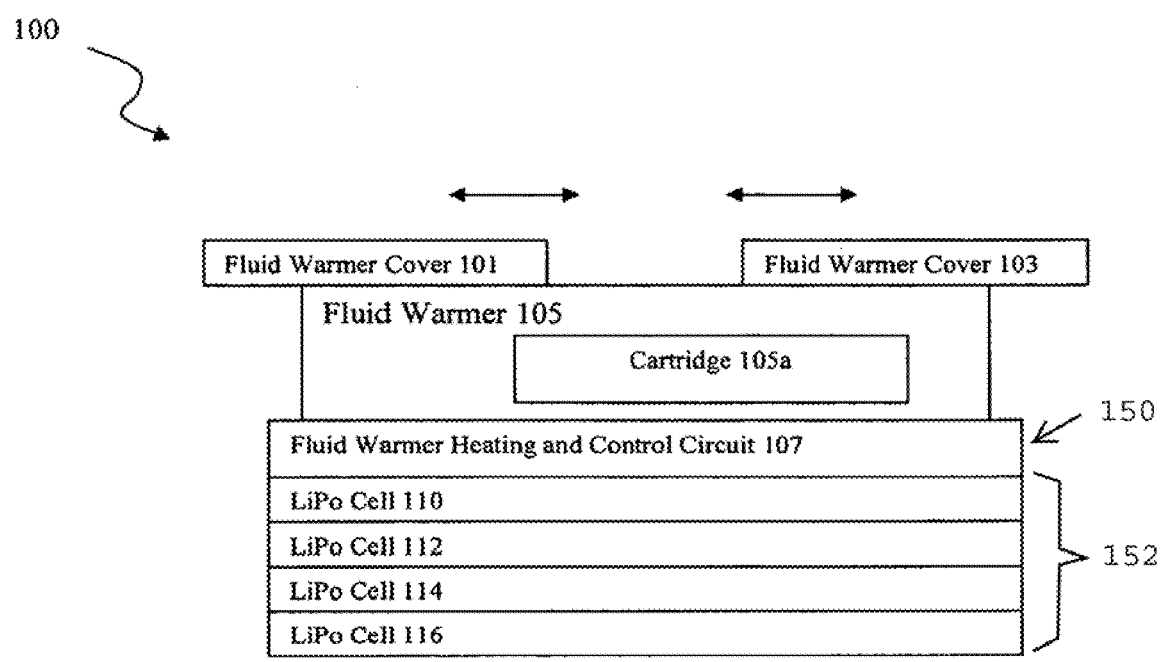
FIG. 1—A fluid warmer assembly according to a first embodiment of the present invention.

FIG. 1 illustrates a fluid warmer assembly 100 according to a first embodiment of the present invention. A fluid warmer 105 has a fluid warmer cover 101 and a fluid warmer cover 103. The arrows above the fluid warmer cover 101 and the fluid warmer cover 103 show the respective bidirectional capability of movement. The fluid warmer cover 101 and the fluid warmer cover 103 include a switch (not shown) that generates a fluid warmer cover closure signal 244, described below, indicating whether the fluid warmer covers 101, 103 are open or closed.

A unitary housing includes the fluid warmer 105, monitoring and control electronics, and the rechargeable cells. Specifically, the fluid warmer 105 is disposed on a fluid warmer heating and control circuit 107, which includes a group of rechargeable Lithium Polymer cells, namely, LiPo cells 110, 112, 114, and 116. In a preferred embodiment, the fluid warmer assembly 100 has a removable cartridge 105a to which a fluid line is attached and through which fluid is caused to flow. The cartridge is typically for a single use and is disposed of after use with a patient. The fluid warmer assembly 100 is typically usable for a period of time that the battery pack is capable of being recharged. However, a person having an ordinary skill in the art would appreciate that there could be several variations to a structural relationship between the various components of the fluid warmer assembly 100 described above.

Figure 2A:
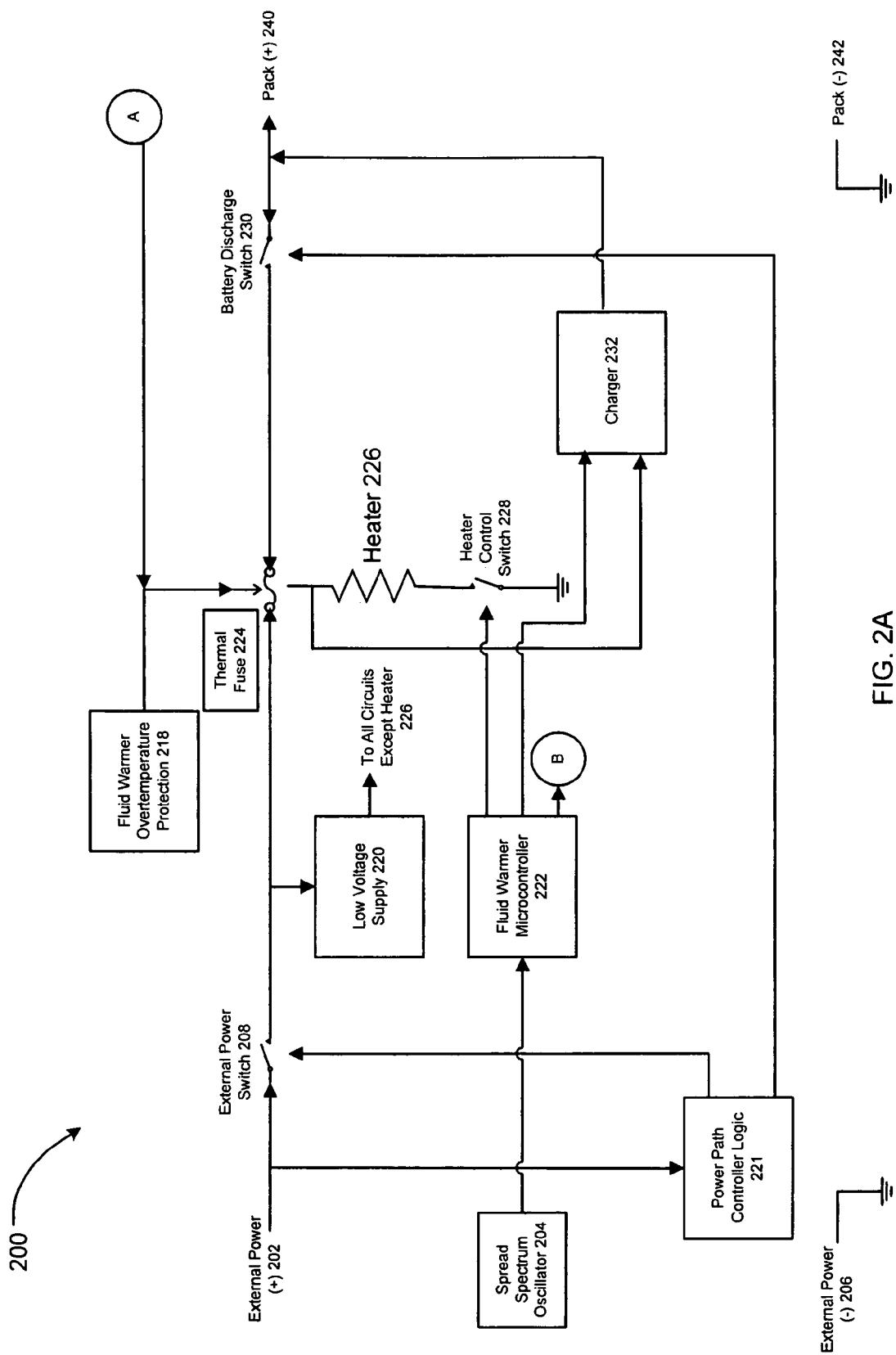
FIG. 2A—A fluid warmer heating and control circuit, part 1 of 2, according to the first embodiment of the present invention.
Figure 2B:
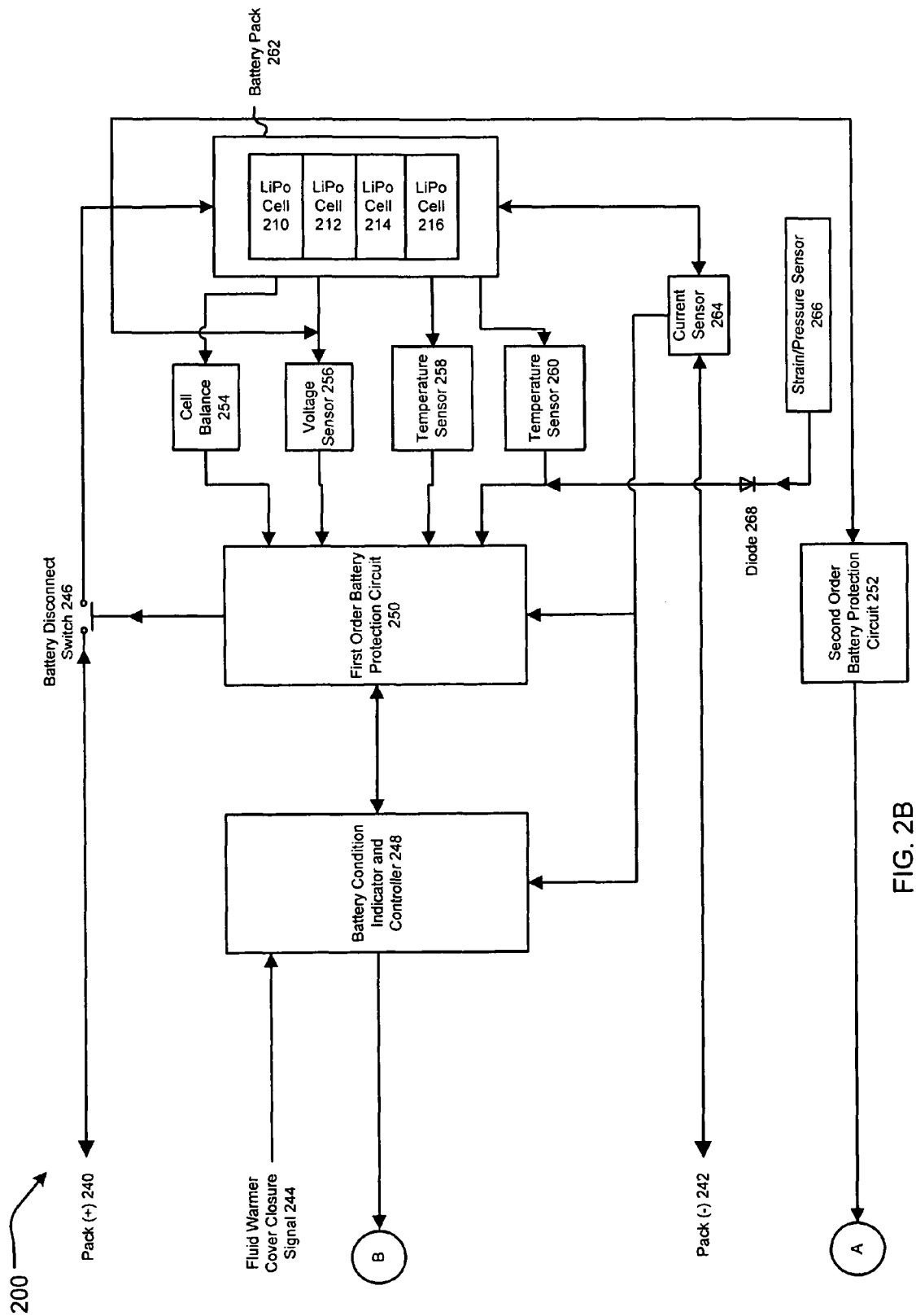
FIG. 2B—The fluid warmer heating and control circuit, part 2 of 2, according to the first embodiment of the present invention.

FIGS. 2A and 2B describe a fluid warmer heating and control circuit 200 according to the first embodiment of the present invention. FIGS. 2A and 2B connect at points A, B, pack(+) 240 and pack(−) 242.

The fluid warmer heating and control circuit 200 is capable of sensing a hazardous condition inside one or more individual cells, such as LiPo cell 210, of battery pack 262. Further, the fluid warmer heating and control circuit 200 permits a magnetic or other isolating coupling of power from a charger 232 to Pack(+) 240. The fluid warmer heating and control circuit 200 has a novel structure that does not permit a conduction of electric power from the battery pack 262 through the charger 232 by including a battery discharge switch 230. That is, electric power from the battery pack 262 to a load does not pass through the charging circuit.

FIG. 2A shows that external power is connected through terminals labeled as external power(+) 202 and external power(−) 206. A power path controller logic 221, akin to steering logic, controls two switches, namely, an external power switch 208 and the battery discharge switch 230 such that based on a need of the fluid warmer assembly 100 or of the battery pack 262, power may be directed from external power or the battery pack 262.

External power(+) 202 is also connected to a low voltage power supply 220 which delivers power to all circuits of the fluid warmer assembly 100 except a heater 226. The heater 226 includes a heating element, adapted to heat a fluid to be administered to a living body in an efficient manner. The heater 226 is controlled by a heater control switch 228 operated by a fluid warmer microcontroller 222.

The heater 226 is powered via a thermal fuse 224 connected to a fluid warmer overtemperature protection circuit 218 and to a second order battery protection circuit 252 shown on FIG. 2B. On sensing a temperature of the fluid warmer 105 exceeding a predetermined limit, the fluid warmer overtemperature protection circuit 218 electrically heats and melts the thermal fuse 224 to prevent an overheating condition. To improve protection, the second order battery protection circuit 252, independent of other protection measures, has been included. On sensing a potentially damaging condition in any of the components of the battery pack 262, the second order battery protection circuit 252 electrically heats and melts the thermal fuse 224 to prevent a furtherance of the potentially damaging condition. A common damaging condition is an excessive voltage across the components of the battery pack 262, namely, LiPo cells 210, 212, 214, and 216 shown on FIG. 2B. Though the second order battery protection circuit 252 is shown connected to the voltage sensor 256, other sensor(s) may also be connected to the second order battery protection circuit 252.

The fluid warmer microcontroller 222 may operate the heater control switch 228 based on a range of conditions stemming from personal safety and circuit operation considerations. A spread spectrum oscillator 204 is included in the fluid warmer heating and control circuit 200 for at least two purposes. A first purpose is to provide for an improved electromagnetic compatibility (EMC) performance. A second purpose is to facilitate, via the fluid warmer microcontroller 222, a pulse width modulation of the charger 232 to control the output voltage or regulate the current of the charger 232. The charger 232 is connected to the battery pack 262 via pack(+) 240. In an alternative embodiment, suitable circuitry included either in the spread spectrum oscillator 204 or the charger 232 may permit a direct connection between the spread spectrum oscillator 204 and the charger 232 for controlling the output voltage or regulating the current of the charger 232. In such an embodiment, charger 232 is connected to battery condition indicator and controller 248 described below.

FIG. 2B also illustrates some additional monitoring and control blocks to facilitate charging and discharging of the battery pack 262. A battery condition indicator and controller 248 may interface with, as shown in FIG. 2B, a first order battery protection circuit 250, a current sensor 264, a fluid warmer cover closure signal 244, and a fluid warmer microcontroller 222. In some embodiments, the battery condition indicator and controller has an electromagnetic interface. In some embodiments, the electromagnetic interface is an electrical interface. In some embodiments, the electromagnetic interface is an optical interface. The battery condition indicator and controller 248 is connected to a first order battery protection circuit 250. The battery condition indicator and controller 248 together with the first order battery protection circuit 250 provide a first-level protection to the LiPo cells, indicate the battery capacity, charge the LiPo cells in a balanced manner, facilitate "sleep" or "wake"-style activation of the LiPo cells, and communicate with external circuits as needed. The operation of the battery condition indicator and controller 248 is activated when a fluid warmer cover closure signal 244 is received. That is, the fluid warmer cover closure signal 244 is generated when the fluid warmer covers 101, 103 operate as shown on FIG. 1. As an example, heating of a fluid in fluid warmer 105 begins when the fluid warmer covers 101, 103 are closed.

The first order battery protection circuit 250 accepts inputs from several sensors to operate a battery disconnect switch 246. These sensors are: voltage sensor 256, temperature sensors 258 and 260, current sensor 264, and strain/pressure sensor 266. These sensors may be connected to one or more of the LiPo cells 210, 212, 214, and 216. Though only four LiPo cells 210, 212, 214, and 216 are shown, more or fewer LiPo cells may be employed based on a given application by making simple changes in the fluid warmer heating and control circuit 200 appreciated by a person having an ordinary skill in the art. In addition to a voltage sensor 256 and a current sensor 264, the first order battery protection circuit 250 also accepts a temperature sensor 258 and a temperature sensor 260. Based on a structure or a layout of the fluid warmer assembly 100 of FIG. 1, the temperature sensor 258 and the temperature sensor 260 may be located at different points on the battery pack 262 to provide a better monitoring, in a distributed manner, of the overall temperature of the battery pack 262. Though not shown on FIGS. 2A and 2B, additional temperature sensors may be provided, for example, to monitor an ambient temperature or a body temperature.

The current sensor 264 is also connected to the battery condition indicator and controller 248 to permit a control of the first order battery protection circuit 250 and facilitate the battery condition indicator and controller 248 to function as a "battery gas gauge." It may also be noted that FIGS. 2A and 2B show the fluid warmer microcontroller 222 and the battery condition indicator and controller 248 as separate blocks but these two may be combined in a single controller.

The first order battery protection circuit 250 is connected to a cell balance circuit 254. The cell balance circuit 254 block monitors various parameters, such as charging/discharging current and terminal voltage. Cell balancing is accomplished by shunting current around one or more of the LiPo cells 210, 212, 214, and 216 in an intelligent manner. That is, current is shunted around a cell which has a higher voltage to an adjacent cell during charging.

The first order battery protection circuit 250 is also connected to a strain/pressure sensor 266 via a diode 268 at a point where the temperature sensor 260 is connected. The diode 286 pulls the temperature sensor 260 low. The strain/pressure sensor 266 is attached to the battery pack 262 in such a manner that the strain/pressure sensor 266 detects a change in a stress or a strain or a pressure relevant to the battery pack 262 or any of the constituent LiPo cells, such as the LiPo cells 210, 212, 214, and 216. Such changes, as well a change in a dimension of the battery pack 262 or any of the constituent LiPo cells, such as the LiPo cells 210, 212, 214, and 216, may herald a potentially harmful condition inside the battery pack 262. An example of change in dimension is a swelling or expansion of an individual cell or the battery pack 262. The first order battery protection circuit 250 operates in response to the signal of the strain/pressure sensor 266, to generate suitable alarms(s) and disconnects the batteries via switch 246.

The fluid warmer heating and control circuit 200 shown in FIGS. 2A and 2B conditions external power to make it usable by the low voltage supply 220, performs pulse width modulation for an intelligent performance of the charger 232, improves the EMC performance, monitors the battery pack 262, via several sensors, for a safe operation, includes a back-up battery protection and a fluid warmer overtemperature protection via the thermal fuse 224. These functions are performed while also sensing the dimensions of the LiPo cells, or the battery pack 262, for a potential structural failure and not permitting a load current from the battery pack 262 to pass through the charger 232 circuitry.

Various circuits or blocks of FIGS. 2A and 2B may be implemented by several commercially available integrated circuits. The spread spectrum oscillator 204 can be based on LTC6908 of the Linear Technology Corporation. A pulse width modulator, to control the charger 232, can be implemented by the MCP1630 of the Microchip Technology, Inc.

The battery condition indicator and controller 248 and the first order battery protection circuit 250 can be implemented by the bq20z70 and the bq29330 chipset of Texas Instruments. The second order battery protection circuit 252 can be implemented by the bq2941x family of Texas Instruments.

The fluid warmer heating and control circuit 200, including the battery pack 262, may be enclosed in a fire- and/or explosion-resistant enclosure (150 depicted in FIG. 1). Alternatively, such an enclosure can contain only the LiPo cells 210, 212, 214, and 216 (152 depicted in FIG. 1). Such enclosure may be rigid or flexible, and composed of a fire- and/or explosion-resistant material such as Kevlar®. A commercially available envelope sold under the brand Liposack is also useful for such an enclosure.

Figure 3:
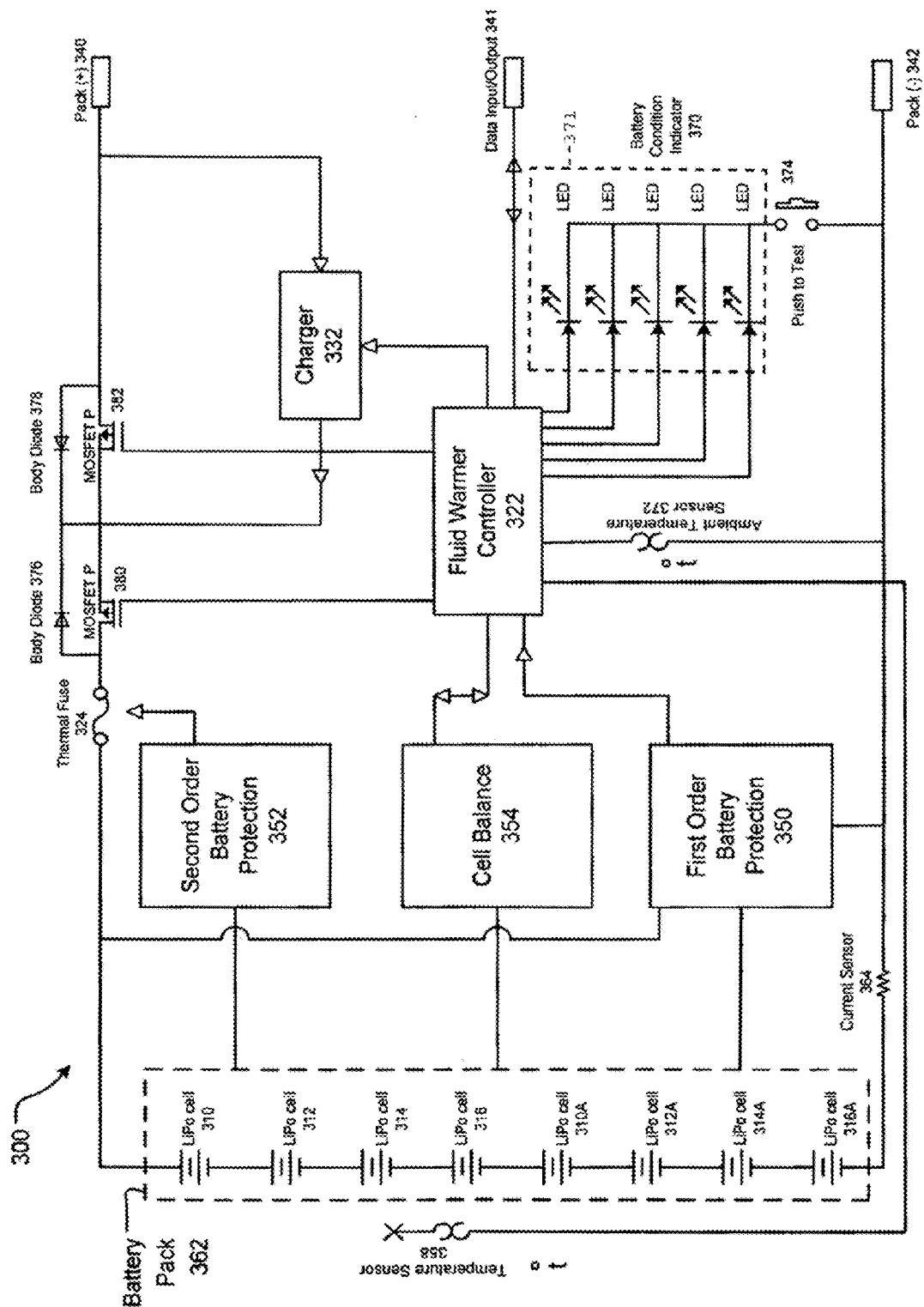
FIG. 3—A fluid warmer heating and control circuit according to a second embodiment of the present invention.

FIG. 3 illustrates a fluid warmer heating and control circuit 300 according to a second embodiment of the present invention. As an illustration, eight LiPo cells, namely, 310, 312, 314, 316, 310A, 312A, 314A, and 316A, are connected in series and included in a battery pack 362. Each of the LiPo cells is connected to a first order battery protection circuit 350, a second order battery protection circuit 352 and a cell balance circuit 354. The first order battery protection circuit 350 and the cell balance circuit 354 are connected to a fluid warmer controller 322 which also receives temperature information from a temperature sensor 358 and from an ambient temperature sensor 372. The fluid warmer controller 322 is in communication with a charger 332. The fluid warmer controller 322 communicates with a controller of an IV fluid warmer system (not shown) via a data input/output 341. A UART included in the fluid warmer controller 322 can be used for data transfer. The fluid warmer controller 322 is also coupled to an array of LEDs, constituting a battery condition indicator 370, which indicates battery charge and also a warning of a hazardous condition. The battery condition indicator 370 may include a display and an annunciator 371. A push-to-test switch 374 is provided for actuation of the battery condition indicator 370.

The LiPo cells 310, 312, 314, 316, 310A, 312A, 314A, and 316A are connected via a current sensor 364 to the negative output terminal labeled Pack(−) 342. The positive output of the stack is connected via a thermal fuse 324 and a pair of MOSFET P 380 and MOSFET P 382 to the positive output terminal labeled Pack (+) 340. The reference numerals 376 and 378 indicate the body diodes inherent with the structure of the respective MOSFET P 380 and MOSFET P 382. The charge and discharge states of the LiPo cells 310, 312, 314, 316, 310A, 312A, 314A, and 316A are continuously monitored by the first order battery protection circuit 350 and the second order battery protection circuit 352 and the charge status is provided to the fluid warmer controller 322. The fluid warmer controller 322 provides control signals to the cell balance circuit 354 operative to adjust the charging and discharging current to LiPo cells 310, 312, 314, 316, 310A, 312A, 314A, and 316A within a safe operating range. In the event of an undesirable condition, such as an abnormally high voltage or a high current or a high temperature, the fluid warmer controller 322 in response to inputs from the first order battery protection circuit 350 and the second order battery protection circuit 352 and/or cell balance circuit 354 and/or from temperature sensor 358 and ambient temperature sensor 372, causes one or both of MOSFET P 380 and MOSFET P 382 to turn off and thereby shut off the supply of current from the LiPo cells 310, 312, 314, 316, 310A, 312A, 314A, and 316A.

The second order battery protection circuit 352 is operative to monitor charge and discharge states of the LiPo cells 310, 312, 314, 316, 310A, 312A, 314A, and 316A and in the event of a fault condition provide an output current to melt the thermal fuse 324 to disconnect the LiPo cells 310, 312, 314, 316, 310A, 312A, 314A, and 316A before a dangerous condition can occur.

The charger 332 is internal to the fluid warmer assembly 100 of FIG. 1 and eliminates a need for a separate or external charger. In addition, the charger 332 can be operative while the fluid warmer assembly 100 is in use if the fluid warmer assembly 100 is connected to an external charging power source. DC power can be provided to the fluid warmer assembly 100 for operating the charger 332.

The fluid warmer controller 322 provides an identification information via the data input/output 341 to the fluid warmer assembly 100 such that the fluid warmer assembly 100 recognizes an appropriate power source for powering the fluid warmer assembly 100.

Figure 4:
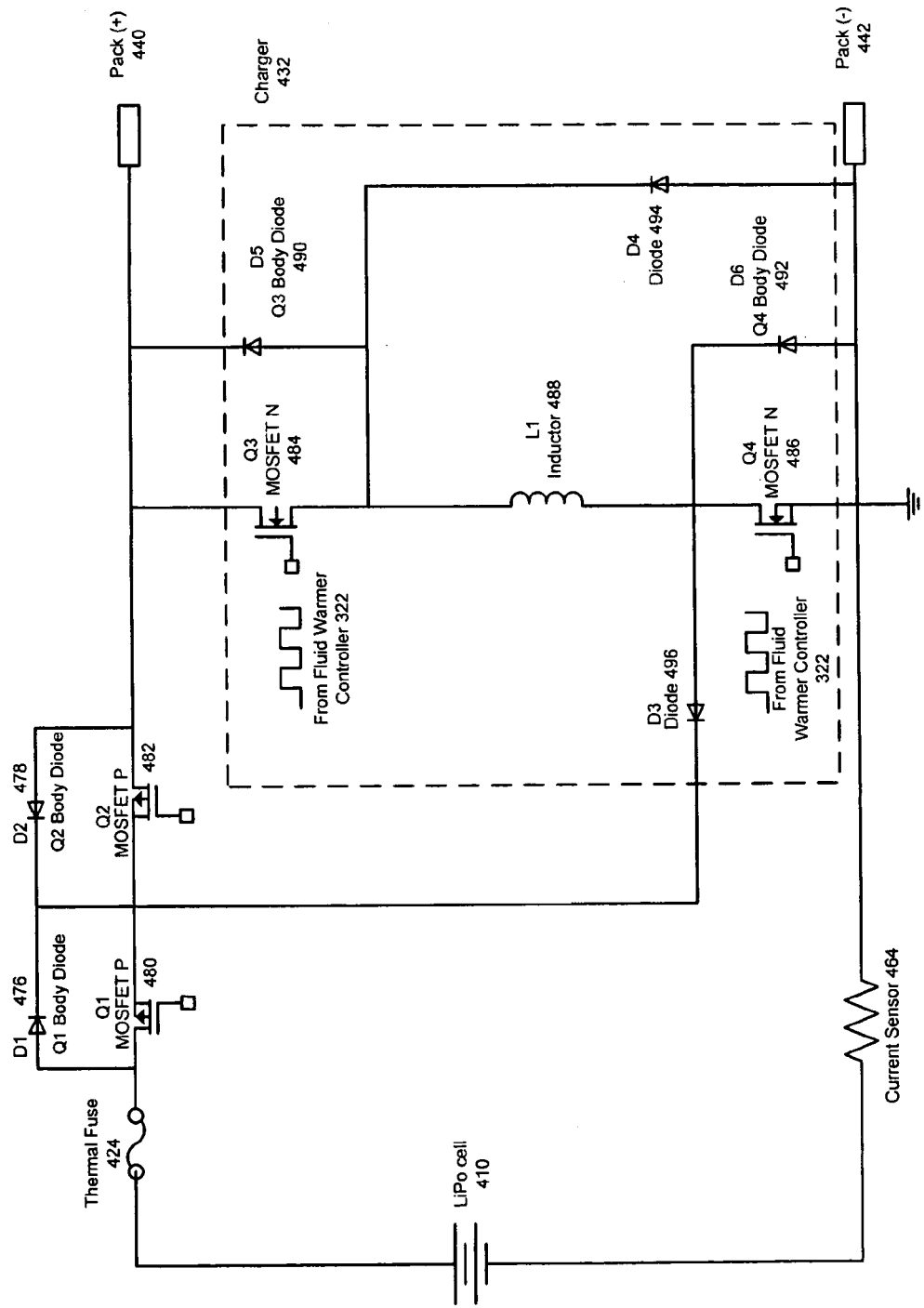
FIG. 4—A charger circuit according to the second embodiment of the present invention.

FIG. 4 illustrates a charger circuit 432 according to the second embodiment of the present invention. Though FIG. 4 shows only one LiPo cell 410, there could be more such LiPo cells based on a specific application.

Similar to the feature of the first embodiment, the charger circuit 432 directs a discharge load current on a path separate from a path of charging current. Specifically, a switch including MOSFET P 480 and MOSFET P 482 connects the LiPo cell 410 to pack(+) 440, via a thermal fuse 424, away from the charging circuitry of charger circuit 432.

When pack(+) 440 and pack(−) 442 are supplied with less than the LiPo cell 410 voltage, a step up conversion is provided by MOSFET N 484, MOSFET N 486, inductor 488 and diode 496. The step up conversion is accomplished under the fluid warmer controller 322 management by holding MOSFET N 484 on and pulsing MOSFET N 486. While MOSFET N 486 is on, current rises in inductor 488, and when MOSFET N 486 turns off, the voltage across inductor 488 reverses polarity and discharges from the pack+ 440 terminal through diode 496 into the battery.

When pack(+) 440 and pack(−) 442 are supplied with battery voltage greater than that of the LiPo cell 410, a step down conversion is provided by MOSFET N 484, MOSFET N 486, inductor 488, diode 496 and diode 494. The fluid warmer controller 322 causes pulsing of both MOSFET N 484 and MOSFET N 486. Current rises in inductor 488 while MOSFET N 484 and MOSFET N 486 are on. When MOSFET N 484 and MOSFET N 486 turn off, the voltage across inductor 488 reverses polarity and discharges through diode 496 into the LiPo cell 410 and from the LiPo cell 410 through diode 494. Alternatively, the diodes 494 and 496 may be replaced with an active switch, such as a MOSFET, for a higher efficiency. Charge current is controlled by measuring the voltage drop across a current sensor 464 and varying the duty cycle of MOSFET N 484 and MOSFET N 486. The reference numerals 476, 478, 490, and 492 indicate the body diodes inherent with the structure of the respective MOSFET P 480, MOSFET P 482, MOSFET N 484, and MOSFET N 486.

The embodiment described above employs a buck-boost converter. A SEPIC converter (Single-ended Primary Inductance Converter) may also be included in the charger circuit 432 in place of the buck-boost converter.

As discussed in relation to FIG. 3, the second order battery protection circuit 352 can interrupt power using the thermal fuse 424 in the event of a major failure such as failure of the MOSFET P 480 or MOSFET P 482, or of the first order battery protection circuit 350.

Though the above description has generally been oriented to powering an IV fluid warmer, a person having an ordinary skill in the art will appreciate that the fluid warmer assembly 100 can also be used for heating other liquids or substances with suitable modifications or enhancements. The invention is not limited to heating IV or other fluids, but is applicable to powering other electrical devices and equipment including other medical devices and equipment.

It will be appreciated by a person having an ordinary skill in the art that modifications to and variations of the above described invention may be made without departing from the inventive concepts disclosed herein. Accordingly, the invention should not be viewed as limited except as by the scope and spirit of the appended claims.

What is claimed is:

1. For use with a system for warming an intravenous fluid to be administered to a living body, which includes a case through which an intravenous fluid line extends, an apparatus comprising:
    a housing configured for attachment to the case, the housing including:
        a plurality of lithium polymer cells;
        a charger connected to the plurality of lithium polymer cells;
        a heater positioned to transfer heat to the case and attached to a thermal fuse;
        a fluid warmer microcontroller connected to the charger and the heater;
        a spread spectrum oscillator connected to the fluid warmer microcontroller;
        a battery condition indicator and controller connected to a fluid warmer cover closure signal and to the fluid warmer microcontroller;
        a first order battery protection circuit connected to elements selected from the group consisting of:
            the battery condition indicator and controller,
            at least one sensor connected to at least one of the plurality of lithium polymer cells,
            a cell balance circuit connected to the at least one of the plurality of lithium polymer cells, and
            a battery disconnect switch;
        a second order battery protection circuit connected to the at least one of the plurality of lithium polymer cells and the thermal fuse; and
        a fluid warmer overtemperature protection to sense the temperature of the case during use and connected to the thermal fuse.

2. The apparatus of claim 1 wherein the case includes a removable cartridge wherein a fluid is caused to flow through the removable cartridge.

3. The apparatus of claim 1 wherein the at least one sensor is a plurality of temperature sensors.

4. The apparatus of claim 3 wherein the plurality of temperature sensors are attached to the plurality of lithium polymer cells in a distributed manner.

5. The apparatus of claim 1 wherein the at least one sensor is a voltage sensor.

6. The apparatus of claim 1 wherein the at least one sensor is a current sensor connected to the battery condition indicator and controller.

7. The apparatus of claim 1 wherein the at least one sensor is a stress sensor.

8. The apparatus of claim 7 wherein the stress sensor includes a diode to pull a temperature sensor low.

9. The apparatus of claim 1 wherein the at least one sensor is a strain sensor.

10. The apparatus of claim 9 wherein the strain sensor includes a diode to pull a temperature sensor low.

11. The apparatus of claim 1 further including a power path controller logic circuit to control an external power switch and a battery discharge switch.

12. The apparatus of claim 1 further including a heater control switch between the fluid warmer microcontroller and the heater.

13. The apparatus of claim 1 further including a battery condition indicator having a display.

14. The apparatus of claim 1 further including a battery condition indicator having an annunciator.

15. The apparatus of claim 1 wherein the charger is coupled to the plurality of lithium polymer cells such that the charger directs a discharge load current on a path separate from a path of charging current.

16. The apparatus of claim 1 wherein the battery condition indicator and controller has an electromagnetic interface.

17. The apparatus of claim 16 wherein the electromagnetic interface is an electrical interface.

18. The apparatus of claim 16 wherein the electromagnetic interface is an optical interface.

19. The apparatus of claim 1 wherein an electric current to warm the case conducts in a circuit separate from the charger.

20. The apparatus of claim 1 further including a fire and/or explosion resistant enclosure containing the battery pack.

21. The apparatus of claim 1 further including a fire and/or explosion resistant enclosure containing the plurality of lithium polymer cells.

* * * * *